(12) United States Patent
Hartley et al.

(10) Patent No.: US 8,545,549 B2
(45) Date of Patent: Oct. 1, 2013

(54) BIFURCATED/BRANCH VESSEL PROSTHESIS

(75) Inventors: David Ernest Hartley, Subiaco (AU);
Robert James Allen, Garran (AU);
Brian Ridley Hopkinson, Nottingham (GB)

(73) Assignee: Cook Medical Technologies LLC, Bloomington, IN (US)

( * ) Notice: Subject to any disclaimer, the term of this patent is extended or adjusted under 35 U.S.C. 154(b) by 2020 days.

(21) Appl. No.: 10/396,676

(22) Filed: Mar. 25, 2003

(65) Prior Publication Data

US 2003/0199967 A1 Oct. 23, 2003

Related U.S. Application Data

(60) Provisional application No. 60/438,345, filed on Jan. 7, 2003.

(30) Foreign Application Priority Data

Mar. 25, 2002 (AU) .................................. PS-1311
Jan. 7, 2003 (AU) .............................. 2003900032

(51) Int. Cl.
*A61F 2/06* (2006.01)
*A61F 2/82* (2006.01)

(52) U.S. Cl.
USPC ................... 623/1.35; 623/1.15; 623/1.13

(58) Field of Classification Search
CPC ............................................... A61F 2/07
USPC .................. 623/1.15–1.22, 1.35, 1.3–1.32
See application file for complete search history.

(56) References Cited

U.S. PATENT DOCUMENTS

| | | | | |
|---|---|---|---|---|
| 5,855,598 A | * | 1/1999 | Pinchuk | 623/1.13 |
| 6,645,242 B1 | * | 11/2003 | Quinn | 623/1.16 |
| 6,673,107 B1 | * | 1/2004 | Brandt et al. | 623/1.35 |
| 6,814,752 B1 | * | 11/2004 | Chuter | 623/1.35 |
| 6,949,121 B1 | * | 9/2005 | Laguna | 623/1.35 |

* cited by examiner

*Primary Examiner* — Jason-Dennis Stewart
(74) *Attorney, Agent, or Firm* — Brinks Hofer Gilson & Lione

(57) ABSTRACT

A stent graft has a tubular wall (1) defining a main lumen with at least one fenestration (15) in the wall. A tube (17) extends from the fenestration into the main lumen and is in fluid communication with the main lumen. An extension leg stent graft can be deployed from a branch vessel into the fenestration to seal into the tube. A flared guide (89) associated with the fenestration can be provided interiorly or exteriorly. There is also disclosed a bifurcated intraluminal prosthesis having a body (1), a first leg (7) and a second leg (17), the first leg extending from the body and the second leg extending into the body.

4 Claims, 8 Drawing Sheets

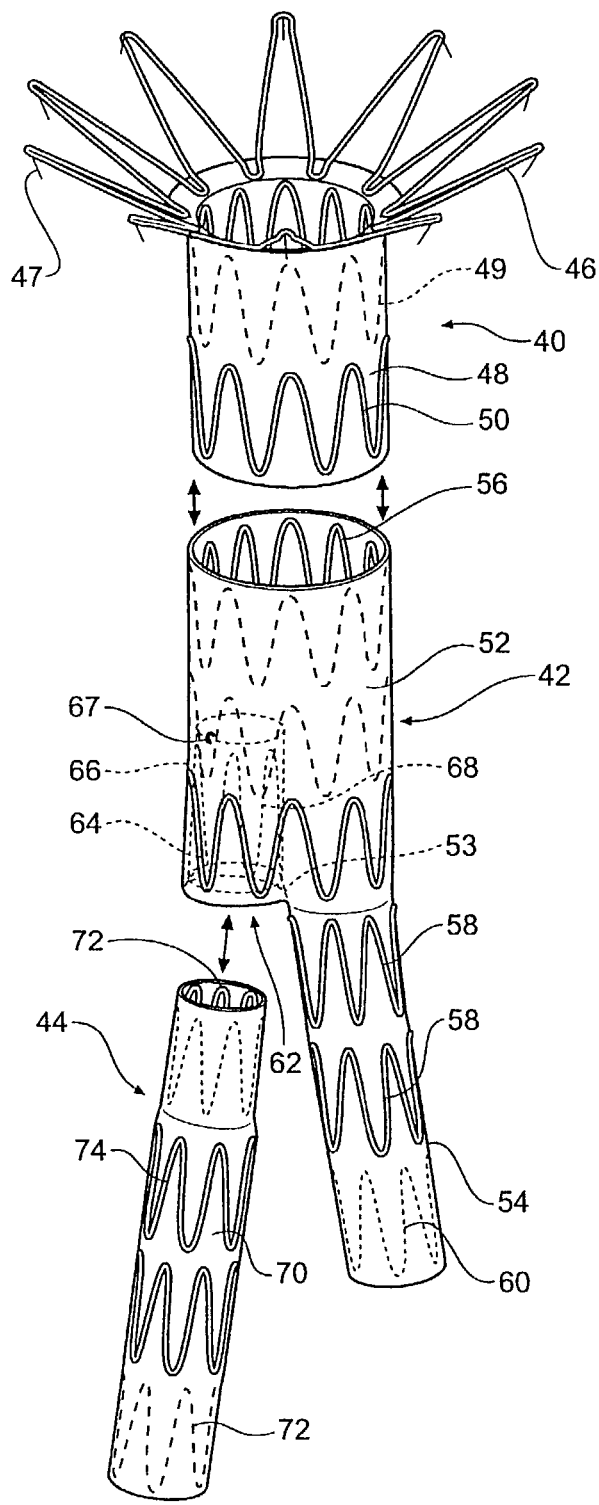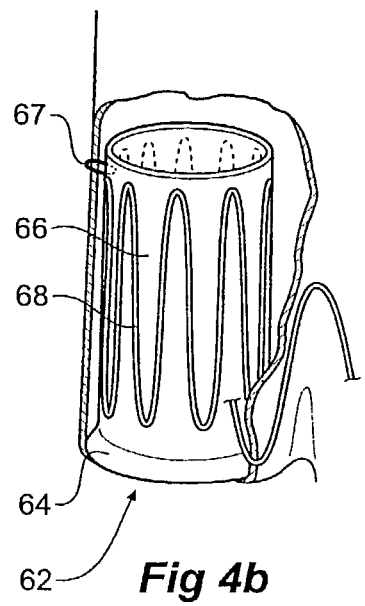
Fig 4a
Fig 4b

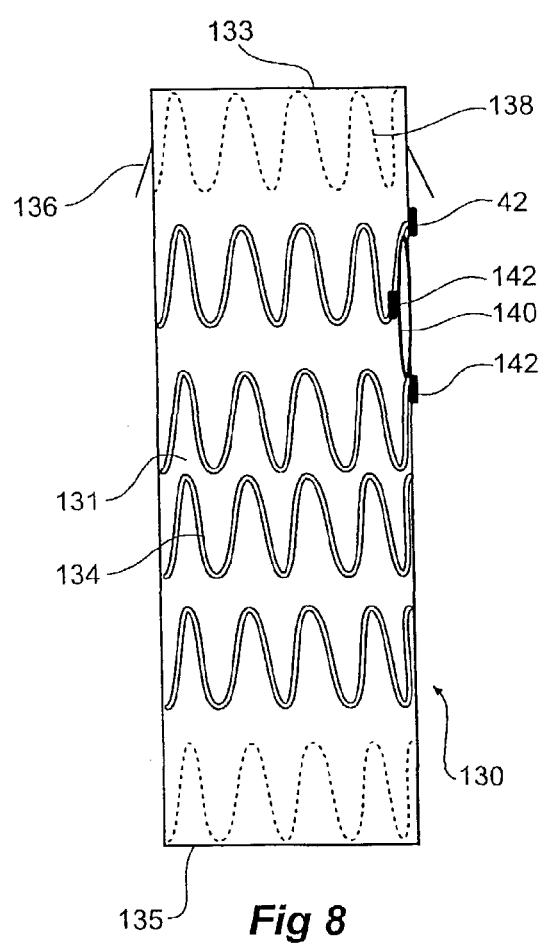
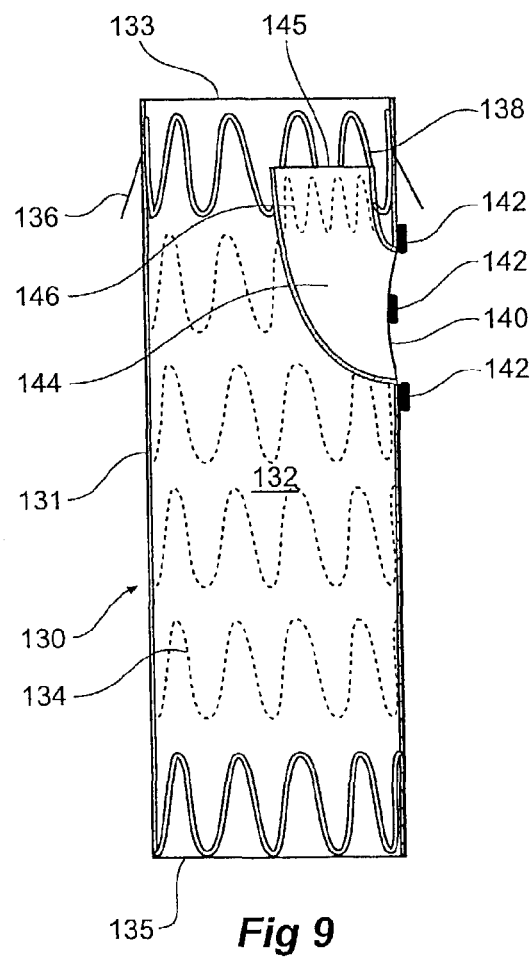
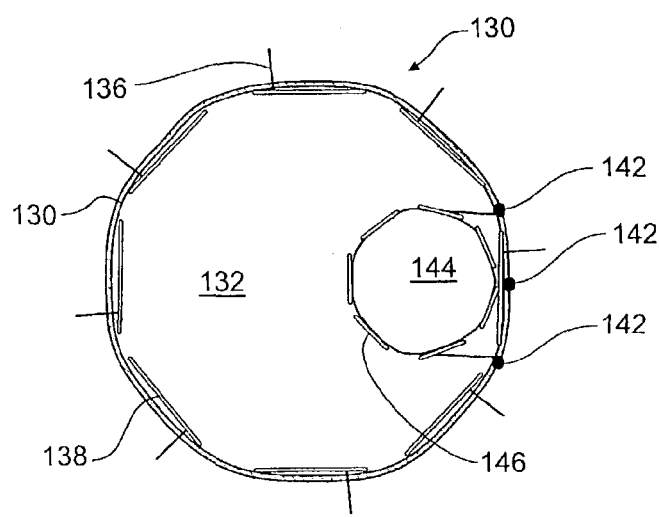

BIFURCATED/BRANCH VESSEL PROSTHESIS

CROSS-REFERENCE TO RELATED APPLICATIONS

This application claims priority to AU Provisional Applications Serial Nos. PS-1311, filed Mar. 25, 2002, 2003900032 filed Jan. 7, 2003, and U.S. Provisional Ser. No. 60/438,345, filed Jan. 7, 2003.

TECHNICAL FIELD

This invention relates to a medical device and in particular to a prosthesis such as a stent graft used in internal body lumens.

BACKGROUND OF THE INVENTION

This invention will be particularly discussed in relation to its application for the repair of abdominal aortic aneurysms and particularly aneurysms adjacent the iliac bifurcation, aneurysms in the thoracic arch and aneurysms in other parts of the aorta where there are branched vessels. The invention is, however, also applicable to other body lumens in humans or animals where a bifurcation or branch vessel is present.

In this specification when referring to the vasculature of a patient the term proximal will be used to define that position or part of a component which is closest to the patient's heart and distal will be used for that position or part of a component which is furthest from the patient's heart. It will be realized that for other body lumens then corresponding terminology such as cranial and caudal should be understood.

A typical bifurcated modular prosthesis usually has a body and a short leg and a long leg extending from the body. Deployment of such a prosthesis at the iliac bifurcation requires placement of the prosthesis in the aorta with the short leg completely contained within the aorta and the long leg extending into one of the iliac arteries. An extension leg is then inserted through the contra-lateral iliac artery into the short leg to complete the bifurcated prosthesis.

Often it is desirable to place the bifurcation of the prosthesis close to the aortic bifurcation but still have enough space for overlap of the extension leg with the short leg in the aorta. In other cases, a graft may need to be placed within another already placed graft and in such case there may only be a short length of grafted aorta to work in. In still other cases there may not be enough space to fit a prosthesis between the renal arteries and the iliac bifurcation and hence for these various situations a new form of bifurcated graft is required.

In the thoracic arch of a human or animal patient there are a number of very important branch arteries which, when treating an aneurysm incorporating the thoracic arch using an endovascular graft, must not be occluded. It is difficult, however, to deploy a stent graft into the thoracic arch with side arms which extend into one or more of the branch arteries from the thoracic arch.

SUMMARY OF THE INVENTION

The foregoing problems are solved and a technical advance is achieved in an illustrative embodiment of the prosthesis of the present invention in which the prosthesis comprises a stent graft having a proximal end, a distal end, a tubular wall defining a main lumen therethrough, at least one fenestration in the wall, and at least one tube extending from the fenestration into the main lumen and in fluid communication with the main lumen. Advantageously, an extension leg stent graft can be deployed from a branch vessel into the fenestration or from the main lumen into the branch vessel and into the tube to seal into the tube.

Preferably as required, the prosthesis comprises multiple fenestrations and multiple tubes extending into the main lumen from the multiple fenestrations.

Preferably the tube extending from the fenestration into the main lumen is angled, curved or bent to extend toward the proximal end of the stent graft. The tube extending and opening towards the proximal end of the graft is directed slightly angled to the longitudinal direction of the main lumen.

Alternatively, the tube or tubes extending from the fenestration into the main lumen is angled, curved or bent to extend toward the distal end of the graft.

The fenestration can be provided with a radiographic or other type of marker around its periphery to enable correct placement of the stent graft with respect to the branch arteries.

In a preferred embodiment of the invention the or each tube includes a flared guide associate with it. In one arrangement the flared guide extends exteriorly of the fenestration and in another arrangement the flared guide extends interiorly of the fenestration.

In one embodiment the tubular wall includes a main wall portion and a leg portion and the fenestration is adjacent a junction between the main wall portion and the leg portion.

Preferably the tube or tubes include self expanding Z stents and the Z stents are preferably on the outside of the tube to provide a smooth inner socket surface into which the extension leg stent graft can be placed to enable sealing therebetween to occur.

To assist with retention, the tube or tubes may be fastened to the interior of the wall at a position spaced apart from the or each fenestration.

The stent graft according to this form of the invention may have a length in the range of 100 to 250 mm with a diameter in the range of 25 to 45 mm. Each fenestration may have a diameter from 5 to 15 mm and the tube may have a length of from 10 to 30 mm. The fenestration may be circular or oval in shape as the leg extension which may be substantially circular may be adapted to enter the fenestration at an angle to normal to the stent graft.

The stent graft may be a portion of a composite stent graft for the aorta in which several separate stent graft portions are connected insitu to provide a longer stent graft.

The distal end of the stent graft may include a distally extending uncovered stent with or without barbs and there may be further provided barbs on the most proximal stent.

It will be seen that by this invention there is provided a stent graft which can be deployed by known endoluminal grafting techniques into the thoracic arch with the fenestrations adjacent one or more of the arteries extending from the thoracic arch and then a leg extension can be deployed via these branch arteries into the fenestration and tube extending into the main lumen from the fenestration to provide a good seal and connection for the leg into the main graft.

It is particularly advantageous to have the tube extending towards the proximal end of the stent graft because it is essential that good blood flow occur into the branch arteries and by having the stent graft directed proximally it enables an opening which faces towards the aortic valve and hence towards the direction of blood flow.

In an alternative embodiment, the invention may be said to reside in an intraluminal prosthesis comprising a stent graft including a substantially tubular body portion providing a body fluid flow path, a first tubular leg extending from the body portion providing a first leg fluid flow path in communication with the body fluid flow path, an aperture in the body adjacent the first tubular leg and a second tubular leg extending from the aperture into the tubular body portion, thereby providing a joining socket for a second leg extension and a second leg fluid flow path in communication with the body fluid flow path.

It will thus be seen that as there is no short leg extending from the body of the prosthesis, the prosthesis can be fitted so that the bifurcation or the point at which the first leg extends from the body can be positioned at the aortic bifurcation and an extension leg can be inserted up an iliac artery to go into the second leg extending into the body, which in fact serves as a socket for the extension leg. Placement of the bifurcation of the prosthesis onto the aortic bifurcation also facilitates location of and insertion of the extension leg.

Preferably the second tubular leg extending into the body includes self expanding Z stents. The Z stents may be on the outside of the second tubular leg to provide a smooth inner socket surface into which a leg extension can be placed to enable sealing therebetween to occur.

In this embodiment of the invention the tube portion extending from the aperture into the body portion may be of sufficient length so that flexibility is provided to a surgeon installing the device and in use the extension leg does not pull out of the second tubular leg.

This embodiment of the invention may further include a flared guide associated with the second tubular leg to provide assistance for access of a deployment device when inserting an extension leg into the prosthesis. In one embodiment the flared guide extends exteriorly of the fenestration and in another embodiment the flared guide extends interiorly of the fenestration.

It will be seen that by this embodiment of the invention the second leg is in effect an inverted leg but that a funnel-like guide is provided extending distally from the bifurcation to give assistance for subsequent access of an extension leg. It will be noted that the flared guide does not necessarily assist with the actual sealing around the extension leg as it is flared but it does assist with access and insertion of the guide wire and deployment device from the contra-lateral artery. The flared guide may include markers to assist with location and placement.

In a further embodiment, the invention is said to reside in a graft prosthesis adapted to span an aortic aneurysm adjacent or including an aortic bifurcation to provide a bypass blood flow path through the aneurysm, the graft prosthesis having a body portion and a tubular leg portion in fluid communication with the body portion, the leg portion adapted to extend into one of the iliac arteries and an aperture in the body portion adjacent to the tubular leg portion, the body portion having a tube portion extending from the aperture into the body portion and in fluid communication with the body portion.

In a still further embodiment, the invention is said to reside in a multi component prosthesis adapted to span an aortic aneurysm adjacent to or including an aortic bifurcation to provide a blood flow path therethrough, the multi component prosthesis comprising:
  a) an upper portion,
  b) a central portion and,
  c) at least one iliac leg extension,
the upper portion having an upper body tube and a plurality of circumferential self expanding Z stents,
the central portion having a body portion and a tubular leg portion in fluid communication with the body portion,
the leg portion adapted to extend into one of the iliac arteries, and an aperture in the body portion adjacent to the tubular leg portion, a tube portion extending from the aperture into the body portion,
the body portion having a plurality of circumferential self expanding Z stents, and
the or each iliac leg extension comprising a tubular graft with a plurality of circumferential self expanding Z stents.

In a still further embodiment, the invention is said to reside in a stent graft comprising a single or multi-part portion to be inserted into and to extend between a first part of a lumen of a patient and a second part, wherein the said portion comprises a first leg section extending from the portion, and wherein the said portion comprises an aperture adjacent to the first leg section with a tube extending from the aperture into the said portion, said tube being for receiving a second leg section.

In a still further form the invention is said to reside in a stent graft comprising a single or multi-part body portion to provide a body portion fluid flow path, a first leg section extending from the body portion to provide a first leg section fluid flow path with the body portion fluid flow path, an aperture in the body portion adjacent to the first leg section with a tube extending from the aperture into the body portion to provide a receiver socket for a second leg section in order to provide a second leg section fluid flow path, also to be in fluid communication with the body portion fluid flow path.

In a still further embodiment, the invention is said to reside in a bifurcated stent graft having a first leg extending from a tubular body and in fluid communication therewith and a second leg also in fluid communication with the body and extending from the bifurcation into the body and a flared guide extending distally from the second leg.

Preferably the second leg is fastened within the tubular body to the wall of the tubular body and the flared guide provides a continuation of the second leg so that there is no discontinuity to inhibit deployment of a guide wire into the second leg via the contra-iliac artery. For this to be achieved the second leg and the flared guide may be made as a single piece of the prosthesis and the sown or otherwise fastened into an aperture into the tubular body at the bifurcation.

In a still further embodiment, the invention is said to reside in a bifurcated intraluminal prosthesis having a body, a first leg and a second leg, the first leg extending from the body and the second leg extending into the body.

The stent grafts of the various embodiments of the invention may have a covering of a bio-compatible material which may be Dacron, expanded polytetrafluoroethylene or other synthetic bio-compatible material.

While Dacron, expanded polytetrafluoroethylene (ePTFE), or other synthetic biocompatible materials can be used to fabricate the coverings for the stent graft and the short side arm, a naturally occurring biomaterial, such as collagen, is highly desirable, particularly a specially derived collagen material known as an extracellular matrix (ECM), such as small intestinal submucosa (SIS). Besides SIS, examples of ECM's include pericardium, stomach submucosa, liver basement membrane, urinary bladder submucosa, tissue mucosa, and dura mater.

SIS is particularly useful, and can be made in the fashion described in Badylak et al., U.S. Pat. No. 4,902,508; Intestinal Collagen Layer described in U.S. Pat. No. 5,733,337 to Carr and in 17 Nature Biotechnology 1083 (November 1999); Cook et al., WIPO Publication WO98/22158, dated May 28, 1998, which is the published application of PCT/US97/14855. Irrespective of the origin of the material (synthetic versus naturally occurring), the material can be made thicker by making multilaminate constructs, for example SIS constructs as described in U.S. Pat. Nos. 5,968,096; 5,955,110; 5,885,619; and 5,711,969. Animal data show that the SIS used in grafts can be replaced by native tissue in as little as a month's time. In addition to xenogenic biomaterials, such as SIS, autologous tissue can be harvested as well. Additionally Elastin or Elastin-Like Polypetides (ELPs) and the like offer potential as a material to fabricate the graft to form a device with exceptional biocompatibility. Another alternative would be to use allographs such as harvested native tissue. Such tissue is commercially available in a cryopreserved state. All of the aforementioned patents, applications and publications are herewith incorporated by reference in its entirety into this specification.

U.S. Pat. No. 5,387,235 entitled "Endovascular Transluminal Prosthesis For Repair Of Aneurysms" discloses apparatus and methods of retaining grafts onto deployment devices. These features and other features disclosed in U.S. Pat. No. 5,387,235 could be used with the present invention and the disclosure of U.S. Pat. No. 5,387,235 is herewith incorporated in its entirety into this specification.

U.S. Pat. No. 5,720,776 entitled "Stent Barb" discloses improved barbs with various forms of mechanical attachment to a stent. These features and other features disclosed in U.S. Pat. No. 5,720,776 could be used with the present invention and the disclosure of U.S. Pat. No. 5,720,776 is herewith incorporated in its entirety into this specification.

PCT Patent Publication No. WO98/53761 entitled "A Prosthesis and a Method of Deploying a Prosthesis" discloses an introducer for a prosthesis which retains the prosthesis so that each end can be moved independently. These features and other features disclosed in PCT Patent Publication No. WO98/53761 could be used with the present invention and the disclosure of PCT Patent Publication No. WO98/53761 is herewith incorporated in its entirety into this specification.

PCT Patent Publication No. WO99/29262 entitled "Endoluminal Aortic Stents" discloses a fenestrated prosthesis for placement where there are intersecting arteries. This feature and other features disclosed in PCT Patent Publication No. WO99/29262 could be used with the present invention and the disclosure of PCT Patent Publication No. WO99/29262 is herewith incorporated in its entirety into this specification.

Australian Provisional Patent Application No. PR8473 entitled "Endoluminal Prosthesis for Curved Lumens" discloses prostheses with arrangements for bending the prosthesis for placement into curved lumens. This feature and other features disclosed in Australian Provisional Patent Application No. PR8473 could be used with the present invention and the disclosure of Australian Provisional Patent Application No. PR8473 is herewith incorporated in its entirety into this specification.

Australian Provisional Patent Application No. PS3244 entitled "Trigger Wires" discloses release wire systems for the release of stent grafts retained on introducer devices. This feature and other features disclosed in Australian Provisional Patent Application No. PS3244 could be used with the present invention and the disclosure of Australian Provisional Patent Application No. PS3244 is herewith incorporated in its entirety into this specification.

Australian Provisional Patent Application No. PS3243 entitled "Thoracic Deployment Device" discloses introducer devices adapted for deployment of stent grafts particularly in the thoracic arch. This feature and other features disclosed in Australian Provisional Patent Application No. PS3243 could be used with the present invention and the disclosure of Australian Provisional Patent Application No. PS3243 is herewith incorporated in its entirety into this specification.

Australian Provisional Patent Application No. PS3215 entitled "A Stent-Graft Fastening Arrangement" discloses arrangements for fastening stents onto grafts particularly for exposed stents. This feature and other features disclosed in Australian Provisional Patent Application No. PS3215 could be used with the present invention and the disclosure of Australian Provisional Patent Application No. PS3215 is herewith incorporated in its entirety into this specification.

Australian Provisional Patent Application No.2002950951 entitled "Asymmetric Stent Graft Attachment" discloses retention arrangements for retaining onto and releasing prostheses from introducer devices. This feature and other features disclosed in Australian Provisional Patent Application No. 2002950951 could be used with the present invention and the disclosure of Australian Provisional Patent Application No. 2002950951 is herewith incorporated in its entirety into this specification.

Australian Provisional Patent Application No. PR9617 entitled "Improving Graft Adhesion" discloses arrangements on stent grafts for enhancing the adhesion of such stent grafts into walls of vessels in which they are deployed. This feature and other features disclosed in Australian Provisional Patent Application No. PR9617 could be used with the present invention and the disclosure of Australian Provisional Patent Application No. PR9617 is herewith incorporated in its entirety into this specification.

BRIEF DESCRIPTION OF THE DRAWING

This then generally describes the invention but to assist with understanding reference will now be made to the accompanying drawings which show preferred embodiments of the invention.

In the drawings:

FIG. 4a shows a still further embodiment of prosthesis according to the invention;

FIG. 4b shows detail of the inverted leg in FIG. 4a;

FIG. 8 shows a side view of a stent graft according to another embodiment of the invention;

FIG. 9 shows a cross sectional view of the stent graft shown in FIG. 8;

FIG. 10 shows an end view of the stent graft shown in FIG. 8;

DETAILED DESCRIPTION

Figure 1:
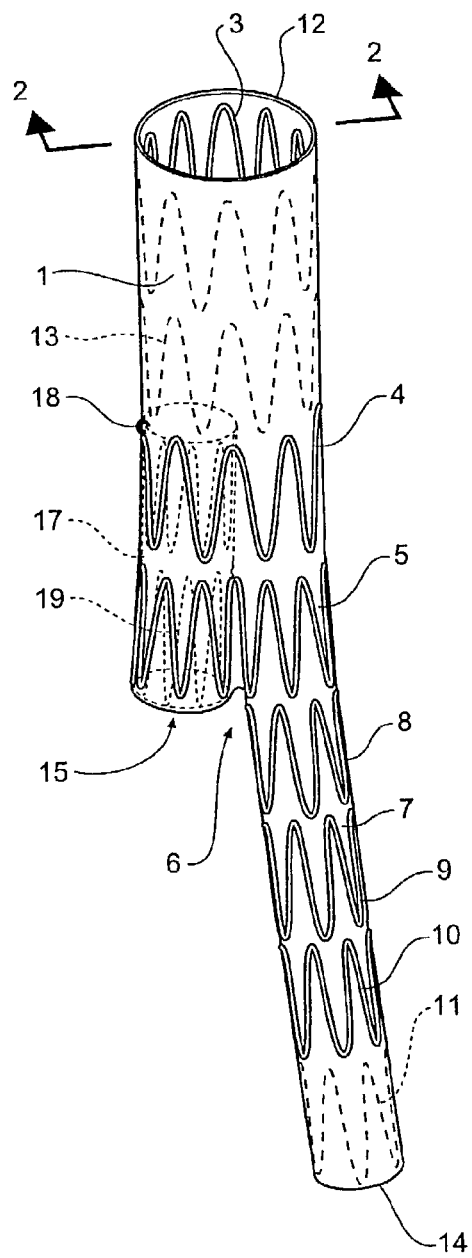
FIG. 1 shows a first embodiment of an intraluminal prosthesis according to the present invention.
Figure 2:
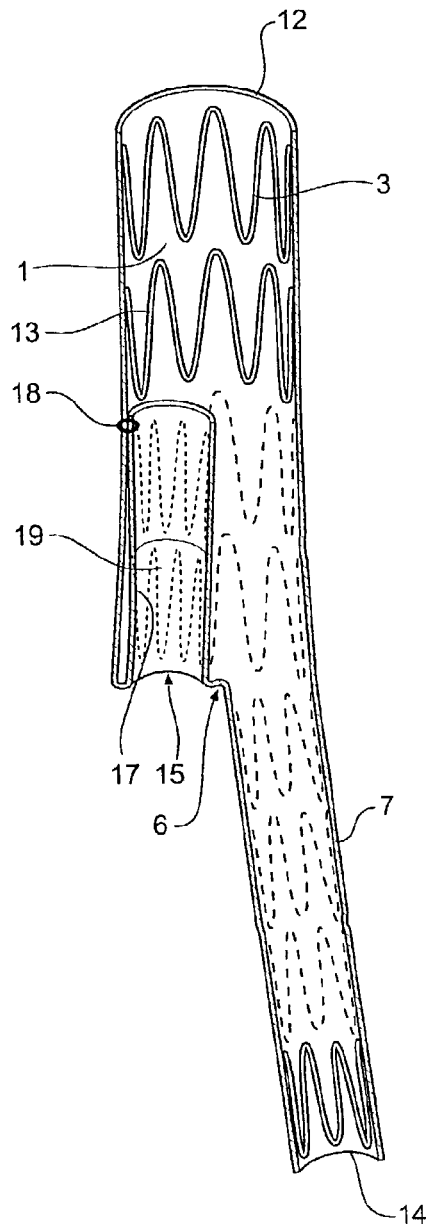
FIG. 2 shows a cut away view of the prosthesis shown in FIG. 1.

Now looking more closely at the drawings and in particular a preferred embodiment shown in FIGS. 1 and 2 there is depicted a prosthesis according to the present invention such as a graft prosthesis; a stent graft; a stent graft prosthesis or assembly; a bifurcated stent graft, prosthesis or assembly; or a multicomponent prosthesis and the like, adapted for deployment adjacent an aortic bifurcation or a branch vessel.

It will be seen that the bifurcated stent graft prosthesis has a body portion 1 with at a proximal end 12 at least one zig zag Z stent 3 and 13 sutured to the inside of the body portion 1. Further zig zag Z stents 4 and 5 are positioned below the proximal end stents 3 and 13 on the outside of the body portion 1. Extending from the body is a first leg 7 with zig zag Z stents 8, 9 and 10 on the outside of the leg and a terminal zig zag Z stent 11 inside the first leg 7 adjacent the distal end 14. The placement of the zig zag Z stents on the inside at the upper and lower ends of the prosthesis provides a good sealing surface where the prosthesis can engage the wall of the vessel lumen into which the prosthesis is inserted. The zig zag Z stents are preferably well-known Gianturco Z stents.

Adjacent to the leg 7 about the bifurcation 6 is an aperture 15 and extending up into the body 1 from the aperture 15 and sealed around the aperture is a second leg tube 17 which provides a socket for an extension leg. The tube 17 is sutured to the wall of the graft body 1 at point 18 proximal of the aperture to hold the tube in place. The tube 17 has at least one zig zag Z stent 19 on its outside surface so that it presents a smooth inner socket surface for insertion of an extension leg.

Figure 3:
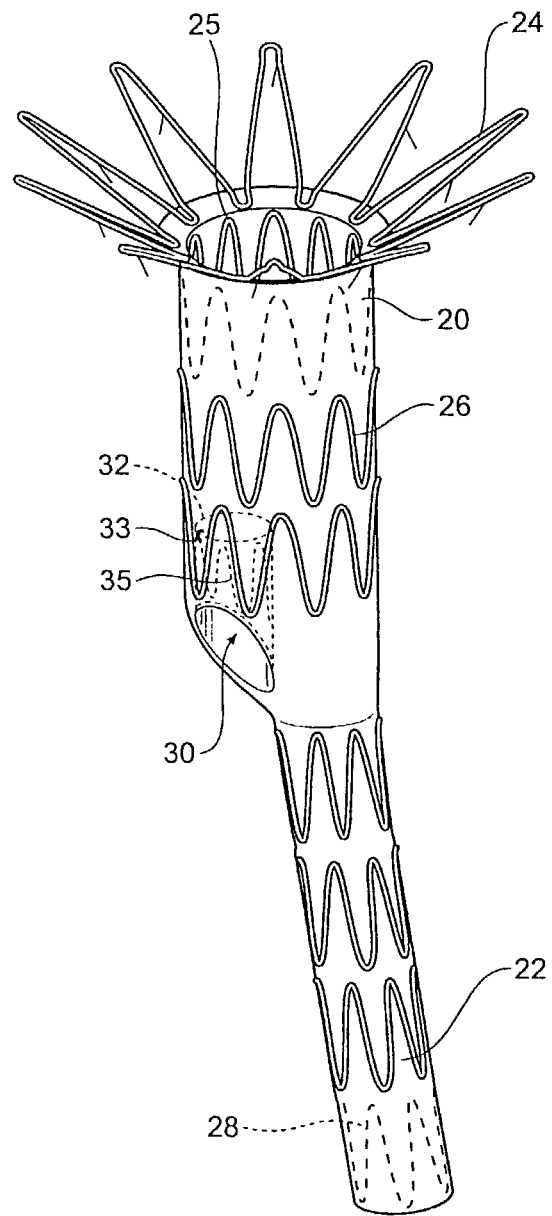
FIG. 3 shows an alternative embodiment of prosthesis according to this invention.

An alternative embodiment of the prosthesis according to the present invention is shown in FIG. 3.

In this embodiment the prosthesis is an aortouni-iliac graft which has a proximal body portion 20 adapted to engage against the wall of an aorta adjacent to the renal arteries and a leg 22 which in use extends down into one of the iliac arteries. The body 20 has a proximal zig zag Z stent 24 extending beyond the top of the body to provide engagement against the walls of the aorta. A further zig zag Z stent 25 is on the inside of the graft body 20 at the proximal end of the prosthesis and subsequent zig zag Z stents 26 are on the outside of the body 20 except the terminal zig zag Z stent 28 on the leg 22 at its distal end which is again on the inside to provide a sealing surface against the iliac artery.

Part way up the graft body 20 is an aperture 30 and extending from the aperture up into the body is a tube 32 to provide a socket for a leg extension for the other iliac artery. The tube 32 is sutured at point 33 to the wall 20 of the graft body so that it remains in place and has zig zag Z stents 35 on its outside surface to provide a good sealing surface within the tube to engage with an extension leg. Stent 35 also helps keep tube 32 open for blood flow therethrough.

A further embodiment of the prosthesis according to this invention is shown in FIGS. 4a and 4b.

The prosthesis, stent graft, graft prosthesis, stent graft assembly, etc. in this embodiment is a multi-component prosthesis system which can be manufactured as an off the shelf item adapted to a range of lengths of aorta. In this embodiment the graft assembly includes an upper portion generally shown as 40, a central portion shown as 42 and a leg extension 44.

The upper portion 40 has a circumferential zig zag Z stent 46 extending from its upper end. This stent preferably includes barbs 47 to ensure secure placement in the aorta. The graft portion 40 has a graft body 48 with a circumferential zig zag Z stent 49 at its proximal end and circumferential zig zag Z stents 50 at its distal end. The upper portion 40 has an essentially tubular graft body.

The central portion 42 has a proximal body portion 52 which is essentially tubular. The central portion also extends from the proximal body portion 52 beyond a bifurcation 53 to a leg 54. The body portion 52 has proximal internal circumferential zig zag Z stents 56 so that the outer surface has a smooth surface to fit inside of and engage the inner surface of the upper portion 40 to provide a sealing engagement. The leg 54 of the central portion 42 has outside stents 58 except an internal stent 60 where the leg is adapted to seal against the wall of the iliac artery.

Adjacent the bifurcation 53 is an aperture 62 with a short conical or funnel shaped portion 64 extending into the body 52 from the aperture and terminating in a substantially cylindrical tubular portion 66 which extends some distance up into the body 52 and provides a socket for sealing of the extension leg portion 44. The funnel portion 64 is provided to assist the insertion of a leg extension after the central portion 42 has been deployed. The tubular portion 66 is fastened to the body 52 at point 67 proximal from the aperture 62 and has a zig zag Z stent 68 on its outer surface as can be seen in the cutaway view of FIG. 4b.

The extension leg portion 44 comprises a substantially tubular body 70 with zig zag Z stents 72 on the inside at its proximal and distal ends and stents 74 on the outside between the proximal and distal ends.

It will be seen that by this system, a multi component prosthesis or stent graft assembly is provided which can be inserted sequentially into the aorta to repair an aneurysm. Normally the upper portion would be deployed first followed by the central portion and finally the leg extension but in some circumstances the central portion could be deployed first followed by the upper portion and then the leg portion. This would require some arrangement of the positions of the inside and outside zig zag Z stents.

Figure 5:
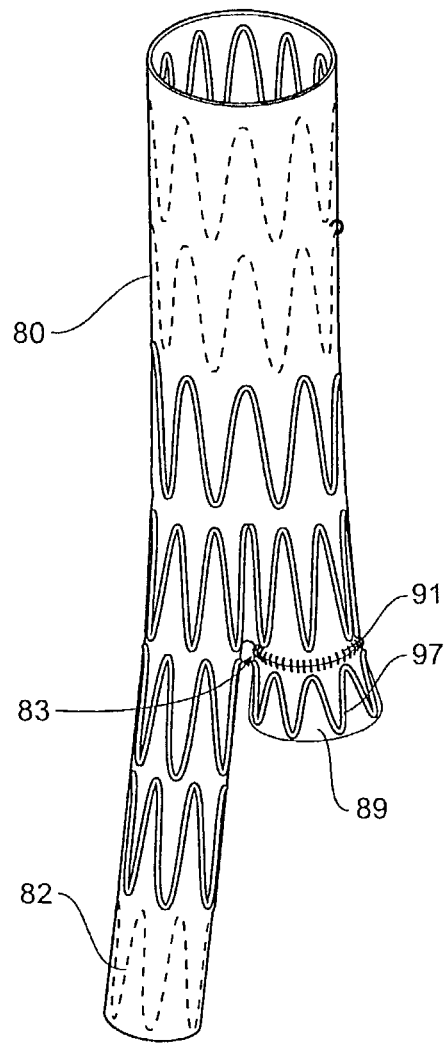
FIG. 5 shows an alternative embodiment of bifurcated stent graft according to the invention.
Figure 6:
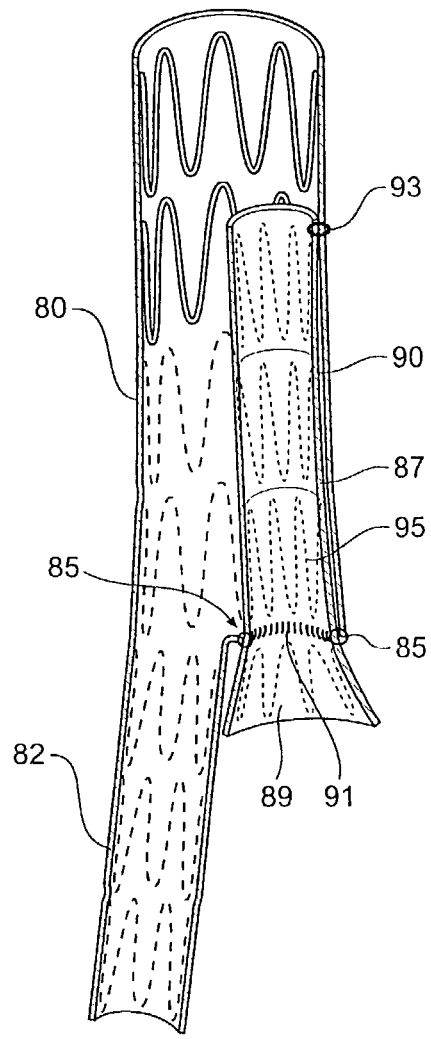
FIG. 6 shows a longitudinal cross section of the embodiment shown in FIG. 5.

A further embodiment of prosthesis or stent graft according to the present invention is shown in FIGS. 5 and 6.

In this embodiment, the prosthesis or stent graft comprises a substantially tubular body portion of 80 of graft material with a first leg 82 extending from a bifurcation at 83 at the distal end of the body portion 80. Adjacent to the bifurcation 83 is an aperture 85 and into the aperture 85 is placed a second leg 87 of graft material. The second leg 87 has a funnel or frusto-conical shape 89 at its distal end and is a substantially cylindrical tube 90 where it extends through the aperture 85 into the body 80. The second leg 87 is sewn into the aperture 85 at 91 and hence presents a substantially uninterrupted inner surface to a guide wire being deployed through the contra-lateral iliac artery during deployment.

It will be noted that like the earlier embodiments of this invention, the prosthesis or stent graft has Gianturco style zig zag Z stents on its inner surface at the ends and other Gianturco style zig zag Z stents on the outside.

The second leg 87 is joined by stitching or other methods at 93 to the inside of the body portion 80. The inner second leg 87 also has Gianturco style zig zag Z stents 95 on its outer surface to again enable a smooth inner surface for deployment of an extension leg into the second leg 87.

The flared guide also has a Gianturco style zig zag Z stent 97 on its outer surface to hold it open and to again provide a smooth inner frusto conical surface for access of the guide wire and subsequently a deployment device and an extension leg into the second leg.

It will be seen that by this embodiment a flared guide is provided to assist with the placement of a guide wire and subsequently a deployment device from the contra-lateral iliac artery into the second leg. The flared guide is sufficiently short that the graft as a whole can be placed down close to the iliac bifurcation to enable efficient catheterization from the contralateral iliac limb.

The use of the endoluminal prosthesis or stent graft of the present invention with a socket within the aortic part of the prosthesis means that the surgeon introducing the leg extension has considerable flexibility in ensuring that the distal cuff on the extension leg is able to be placed in a selected position because of good overlap length of the extension leg within the socket.

Figure 7:
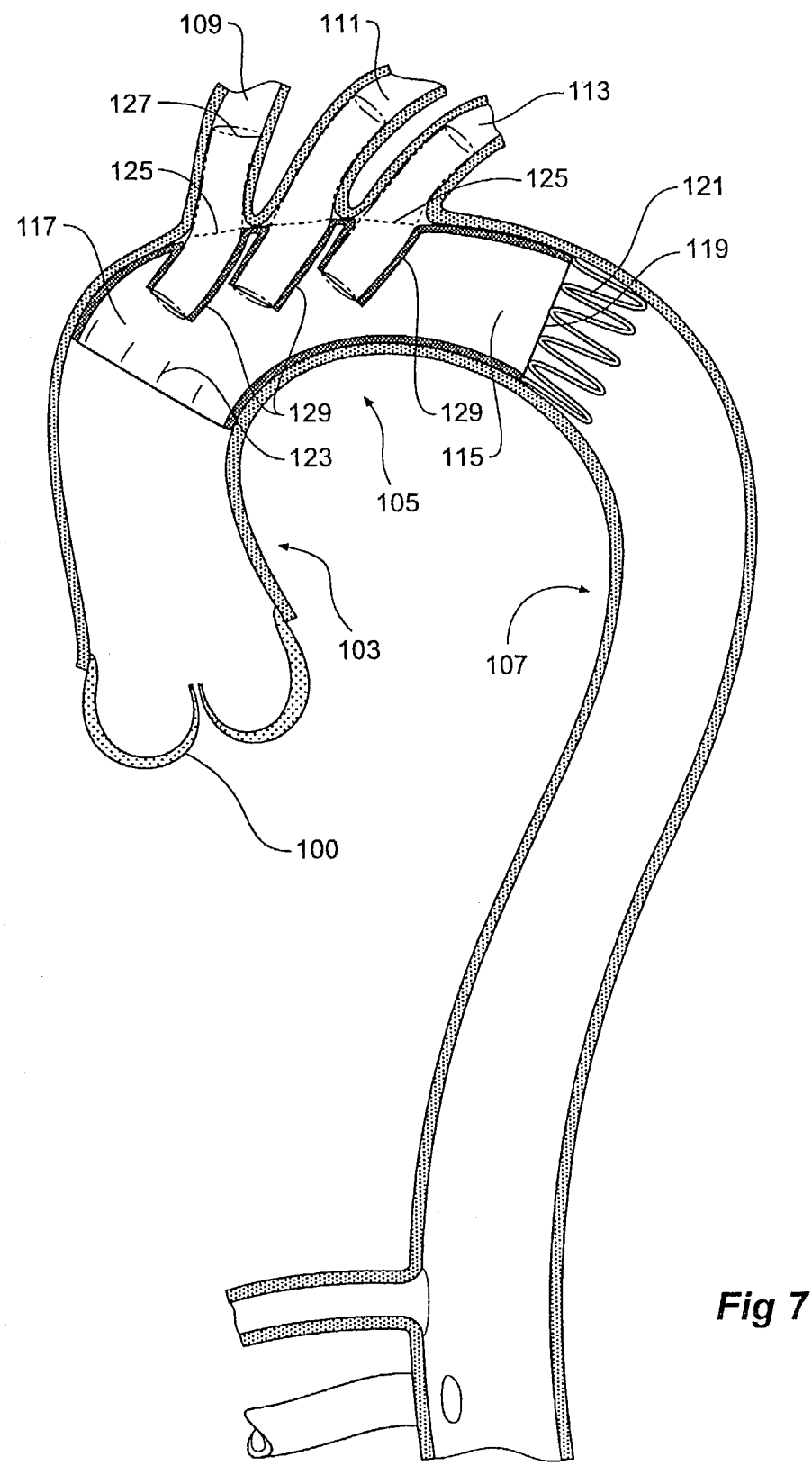
FIG. 7 shows a schematic view of a thoracic arch portion of a human aorta showing placement of a stent graft according to another embodiment of the invention.

FIGS. 7 to 11 show the use of alternative embodiments of a prosthesis or stent graft of the present invention in the thoracic arch of a patient. FIG. 7 shows a schematic view of a thoracic arch portion of a human aorta showing placement of a stent graft according to another embodiment of the invention.

Now looking at FIG. 7 it will be seen that an aorta includes an aortic valve 100 from the heart of a patient, an ascending aorta 103, an aortic arch generally shown as 105 and a descending aorta 107. From the aortic arch 105 extend branch arteries including the innominate artery 109, the left carotid artery 111 and the left subclavian artery 113.

A stent graft 115 is deployed into thoracic arch. The stent graft 115 has a proximal end 117 and a distal end 119. At the distal end 119 is a distally extending uncovered stent 121 to assist with retention of the stent graft in the aorta and at the proximal end 117 are barbs 123 extending through graft material of the stent graft 115 and adapted to engage the wall of the aorta to securely hold the stent graft in position. In the stent graft 115 are fenestrations 125 in positions relative to the innominate artery 109, the left carotid artery 111 and the left subclavian artery 113 respectively such that a leg extension graft 127 shown dotted in FIG. 7 can be deployed via the respective branch arteries into the fenestrations 125. Each fenestration 125 has a tube 129 extending from it into the main lumen of the stent graft 115 and angled, curved or bent towards the proximal end 117 of the stent graft 115. It will be noted, too, that each tube 129 has an open end which is directed towards the proximal end 117 of the stent graft and hence towards the aortic valve 100 where blood flow occurs from the heart. This enables each of the arteries to collect blood as is required without swirling, turbulence or blind spots which could cause thrombosis to occur.

An alternative embodiment of the prosthesis or stent graft according to this invention is shown in FIGS. 8 to 10. The stent graft 130 includes a tubular body 131 defining a main lumen 132. There are a number of Gianturco style zig zag Z stents 134 in the tubular body with stents at the proximal and distal ends inside the graft and outside the graft between the proximal and distal ends. Barbs 136 extend from the most proximal stent 138.

In the side of the body 131 is a fenestration 140. A plurality of radiographic markers 142 are provided around the fenestration 140 to assist with location of the stent graft within the human or animal body using suitable radiographic techniques.

Extending from the fenestration 140 into the main lumen 132 is a tube 144. The tube 144 is angled, curved or bent to extend towards the proximal end 133 of the stent graft 130. The tube 144 is in fluid communication with the main lumen via open end 145. The tube 144 also has a Gianturco style zig zag Z stent 146.

As is illustrated particularly in FIG. 7 a leg extension can be deployed into the tube 144 from the side branch artery to seal into the tube 144 to allow blood flow from the ascending aorta and aortic arch into the respective arteries.

Deployment of the leg extension stent graft into the fenestration and the tube from the side branch artery can use access via left or right brachial arteries or the carotid arteries as required by known endovascular techniques.

Figure 11A:
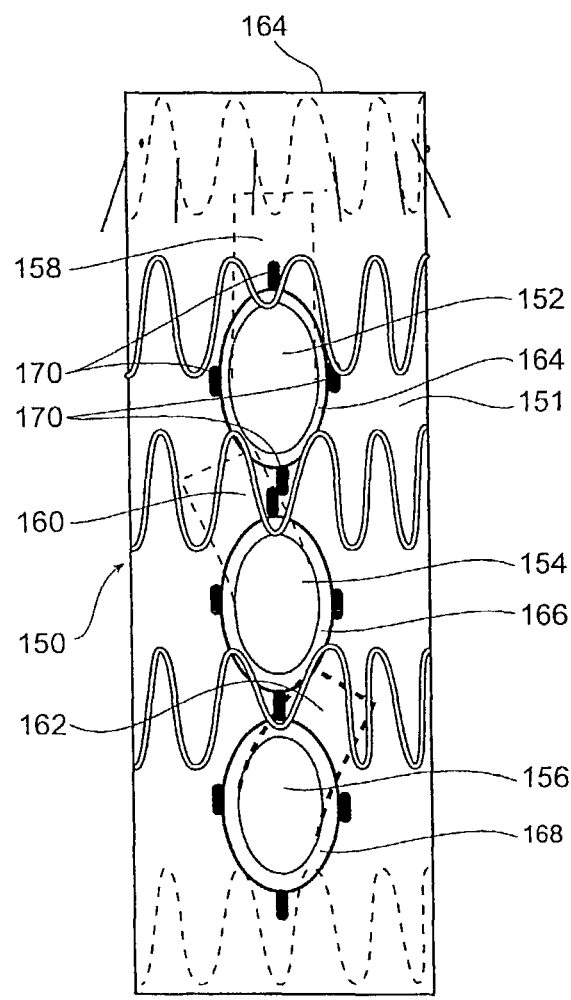
FIG. 11 shows a side view of an alternative embodiment of stent graft according to this invention.
Figure 11B:
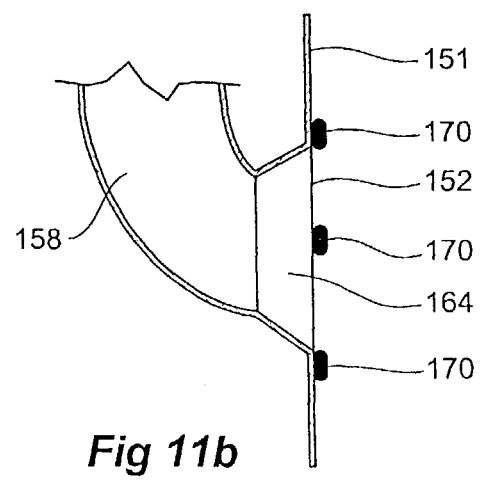

FIGS. 11a and 11b show an alternative embodiment of the prosthesis or stent graft 150 according to this invention. In this embodiment, the body 151 of the stent graft 150 has three fenestrations 152, 154 and 156. From each fenestration 152, 154 and 156 there is a tube 158, 160 and 162 respectively which is angled, bent or curved and directed towards the proximal end 64 of the stent graft. With respect to the tubes 160 and 162 these are directed slightly sideways or angled to the longitudinal direction of the stent graft 150 so that their open ends can receive blood flow without problems with blind flow spots in the grafted aortic arch.

It will be noted, too, that between the fenestrations 152, 154 and 156 and the tubes 158, 160 and 162 the are flared guides 164, 166 and 168 respectively to provide a guide for the deployment of a guide wire from the respective branch artery as discussed above. In a case where the stent graft is deployed in an aneurysmal sac there may be sufficient space between the stent graft main body and the wall of the vessel for the flared guides to be positioned exteriorly of the stent graft main body.

FIG. 11b shows a detail of the fenestration 152 in a wall of the stent graft body 151 particularly showing the flared guide 164 between the fenestration 152 and the tube 158.

Around each of the fenestrations 152, 154 and 156 there are radiopaque markers 170 to assist with correct placement of the stent graft in the thoracic arch.

Figure 12:
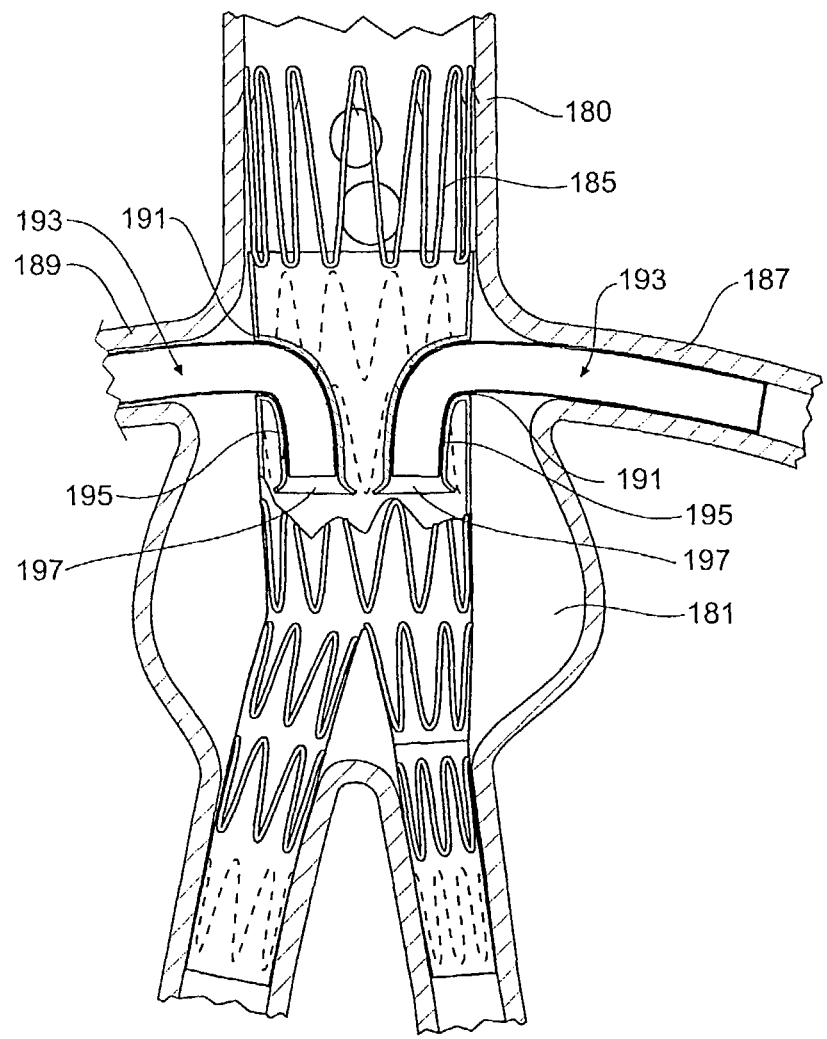
FIG. 12 shows a schematic view of a human aorta in the region of the renal arteries showing placement of a stent graft according to another embodiment of the invention.

FIG. 12 shows a schematic view of a human aorta in the region of the renal arteries showing placement of a prosthesis or stent graft according to another embodiment of the invention.

In FIG. 12 the aorta 180 has an aneurysmal sac 181 and a stent graft 183 according to this embodiment of the invention has been deployed into the aneurised space. The main graft 183 has super-renal uncovered stent 185 which is received in a non-aneurised region of the aorta 180 and provides a top support for the main graft 183. The main aneurised region 181, however, extends up past the renal arteries 187 and 189 and as such is necessary to provide side branch grafts to these arteries.

For this purpose there are fenestrations 191 provided into the main graft and it is through these fenestrations that the side branch stent grafts 193 extending into the renal arteries 187 and 189 are deployed. To assist with deployment of the side branch stent grafts 193 a tube 195 is provided from each of the fenestrations 191 and extending towards the distal end of the main stent graft 183. At the distal end of the tubes 195 there is a flared guide 197 to assist with the deployment of a guide wire from the main graft 183 into the respective tubes 195.

Throughout this specification various indications have been given as to the scope of this invention but the invention is not limited to any one of these but may reside in two or more of these combined together. The examples are given for illustration only and not for limitation.

Throughout this specification and the claims that follow unless the context requires otherwise, the words 'comprise' and 'include' and variations such as 'comprising' and 'including' will be understood to imply the inclusion of a stated integer or group of integers but not the exclusion of any other integer or group of integers.

What is claimed is:

1. A prosthesis comprising a stent graft including a substantially tubular body portion of a first diameter to engage against the wall of an aorta providing a body fluid flow path through the tubular body portion, the tubular body portion comprising an interior surface, a first tubular leg being of substantially lesser diameter than the tubular body portion to extend down into an iliac artery extending from the body portion and the first tubular leg being affixed to the tubular body portion and providing a first leg fluid flow path in communication with the body fluid flow path, an aperture in the tubular body portion adjacent the first tubular leg and a second tubular leg of substantially the same diameter as the first tubular leg and the second tubular leg being affixed to the tubular body portion, the second tubular leg extending from the aperture in a direction into the tubular body portion, the second tubular leg comprising a second leg fluid flow path and the second leg fluid flow path being in fluid communication with the body fluid flow path through the tubular body portion, the second tubular leg comprising self expanding Z stents and the self expanding Z stents being on the outside of the second tubular leg to provide a smooth inner socket surface and a suture material fastening between the second tubular leg and the interior surface of the tubular body portion at a position proximal of the aperture, and a flared guide at the aperture in the tubular body and being associated with the second tubular leg to provide assistance for access of a deployment device when inserting an extension leg into the prosthesis, the second tubular leg thereby providing a joining socket for a leg extension.

2. A prosthesis as in claim 1 wherein the second tubular leg extending from the aperture in the body portion comprises two self expanding stents whereby it is of sufficient length so that flexibility is provided to a surgeon installing the device and in use the extension leg does not pull out of the second tubular leg.

3. A prosthesis as in claim 1 wherein the flared guide extends exteriorly of the aperture.

4. A prosthesis as in claim 1 wherein the flared guide extends interiorly of the aperture.

* * * * *